United States Patent
Wu et al.

(10) Patent No.: US 10,398,735 B2
(45) Date of Patent: Sep. 3, 2019

(54) COMPOSITIONS AND METHODS FOR PRODUCING RECONSTITUTED SKIN

(71) Applicant: ADERANS RESEARCH INSTITUTE, INC., Beverly Hills, CA (US)

(72) Inventors: Xunwei Wu, Medford, MA (US); Kurt Stenn, Princeton, NJ (US); Larry Scott, Jr., Willingboro, NJ (US); Daniel J. Hussey, Atlanta, GA (US)

(73) Assignee: ADERANS RESEARCH INSTITUTE, INC., Beverly Hills, CA (US)

( * ) Notice: Subject to any disclaimer, the term of this patent is extended or adjusted under 35 U.S.C. 154(b) by 190 days.

(21) Appl. No.: 15/597,416

(22) Filed: May 17, 2017

(65) Prior Publication Data
US 2017/0246213 A1  Aug. 31, 2017

Related U.S. Application Data

(62) Division of application No. 14/059,240, filed on Oct. 21, 2013, now Pat. No. 9,655,930.

(60) Provisional application No. 61/708,221, filed on Oct. 1, 2012.

(51) Int. Cl.
| | |
|---|---|
| A61K 35/36 | (2015.01) |
| C12N 5/071 | (2010.01) |
| C12N 5/0775 | (2010.01) |
| G01N 33/50 | (2006.01) |
| A61L 27/18 | (2006.01) |
| A61L 27/38 | (2006.01) |
| A61L 27/60 | (2006.01) |

(52) U.S. Cl.
CPC .............. *A61K 35/36* (2013.01); *A61L 27/18* (2013.01); *A61L 27/3804* (2013.01); *A61L 27/3813* (2013.01); *A61L 27/3834* (2013.01); *A61L 27/60* (2013.01); *C12N 5/0625* (2013.01); *C12N 5/0668* (2013.01); *C12N 5/0698* (2013.01); *G01N 33/5082* (2013.01); *A61L 2430/18* (2013.01); *G01N 2500/10* (2013.01)

(58) Field of Classification Search
None
See application file for complete search history.

(56) References Cited

U.S. PATENT DOCUMENTS

| 8,211,694 B2 | 7/2012 | Stahl |
| 2010/0227397 A1 | 9/2010 | Kishimoto |
| 2011/0321180 A1 | 12/2011 | Lee |
| 2012/0095445 A1 | 4/2012 | Zheng |
| 2012/0148541 A1 | 6/2012 | Lee et al. |

FOREIGN PATENT DOCUMENTS

| JP | 2008-125540 A | 6/2008 |
| WO | 2011056017 | 5/2011 |
| WO | 2011160055 A2 | 12/2011 |

OTHER PUBLICATIONS

Integra Bilayer Matrix Wound Dressing "Product Description and Benefits", 2010. Retrieved from internet on Sep. 30, 2015: http://www.ilstraining.com/bmwd/bmwd/bmwd_it_01.html.
Corning "Surface Areas and Recommended Medium Volumes for Corning® Cell Culture Vessels", Sep. 2008. 4 pages.
Chapman, et al., "Human keratinocytes are efficiently immortalized by a Rho kinase inhibitor", J Clin Invest, 120:2619-26 (2010).
Chuong, et al., "Defining hair follicles in the age of stem cell bioengineering", J Invest Derm, 127:2098-2100 (2007).
Ehama, et al., "Hair follicle regeneration using grafted rodent and human cells", Soc Inv Derma., 127:2098-2114 (2007).
Guo, et al., "Slug and Sox9 cooperatively determine the mammary stem cell state", Cell, 148:1015-28 (2012).
Kang, et al., "Sphere formation increases the ability of cultured human dermal papilla cells to induce hair follicles from mouse epidermal cells in a reconstitution assay", Soc Inv Derma., 132:237-9 (2012).
Lee, et al., "A simplified procedure to reconstitute hair-producing skin", Tissue Eng., 17(4):391-400 (2011).
Li, et al., "Human TSC2-null fibroblast-like cells induce hair follicle neogenesis and hamartoma morphogenesis", Nat. Commun., 2:1-17 (2011).
Rizzino, "Stimulating progress in regenerative medicine: improving the cloning and recovery of cryopreserved human pluripotent stem cells with ROCK inhibitors", Regen Med., 5(5):799-807 (2010).
Soma, et al., "Hair-inducing ability of human dermal papilla cells cultured under Wnt/$^2$-catenin signaling activation", Exp. Derma., 21:299-319 (2012).
Vishnubalaji, et al., "In vitro differentiation of human skin-derived multipotent stromal cells into putative endothelial-like cells", BMC Dev Biol., 12:7 (2012).
Yang and Cotsarells, "Review of hair follicle dermal cells", J Dermatol Sci., 57(1):1-19 (2009).
Communication, dated Jan. 23, 2019, issued by the United States Patent and Trademark Office in U.S. Appl. No. 15/597,549.

*Primary Examiner* — Allison M Fox
(74) *Attorney, Agent, or Firm* — Sughrue Mion, PLLC

(57) ABSTRACT

Compositions and methods for producing reconstituted human skin and/or hair follicles in situ are provided. The method for producing the skin is unique in that tissue culture expanded cells including multipotent cells such as neonatal cells as well as cultured epidermal and dermal cells are immediately placed on a substrate such as a membrane and then the membrane with adherent cells is placed on a skin wound. Examples demonstrate formation of hair follicles in situ.

15 Claims, No Drawings

COMPOSITIONS AND METHODS FOR PRODUCING RECONSTITUTED SKIN

CROSS REFERENCE TO RELATED APPLICATIONS

This is a Divisional of U.S. patent application Ser. No. 14/059,240, filed Oct. 21, 2013, which claims the benefit of U.S. Provisional Application No. 61/708,221, filed Oct. 1, 2012. The entire disclosures of the prior applications are considered part of the disclosure of the accompanying divisional application, and are hereby incorporated by reference.

FIELD OF THE INVENTION

The invention is generally related to the field of tissue engineering, in particular to reconstituted skin and methods of use thereof.

BACKGROUND OF THE INVENTION

The ability to reconstitute adult skin with functional skin appendages has long been a major clinical objective for dermatologists and surgeons because reconstituted skin can be used to treat skin wounds or disorders with reduced scarring and enhanced cosmetic appeal (Lee et at., Tissue Engineering: Part C, 17:(4) 391-400 (2011)). Skin damage and loss can occur for many different reasons, such as genetic disorders, chronic wounding or acute trauma such as burns. The damage can be substantial with no possibility of skin regeneration. Burn wounds in particular can be deep and extensive and can often be fatal in the absence of treatment. Currently, the most common treatment method for burn victims includes surgery to facilitate wound closure, followed by autologous skin grafting, where epidermis from an undamaged site is harvested and applied to the full-thickness wound. However, there are significant limitations to these procedures and the repair and management of full-thickness skin damage resulting from burns is still a significant clinical challenge (Shevchenko et al., *J Royal Soc*, 7:229 (2009); Juhasz et al., *Derm Res Prac*, 2010: 210150 (2010)).

Tissue engineering to treat hair loss involves transplanting tissue grafts or cells into the target area to induce hair follicle formation. Hair follicle induction and growth requires active and continuous epithelial and mesenchymal interactions (Stenn and Paus, *Physiol Reviews*, 81:449-494, (2001)). However, not all cells obtained from hair follicle grafts are capable of inducing new hair follicle formation.

Previous studies have shown that isolated hair follicles from human scalp can be grafted onto the backs of immunodeficient mice and subsequently successfully return to normal cycling (Hashimoto et al., *J invest Derm* 115:200 (2000)). Human hair follicle formation by grafting a skin substitute incorporated with cultured mutant (NCH deficient) fibroblast cells has been reported (Li et al., *Nat Comm*, 2:235 (2010)). However, the regenerated hair follicle did not produce outgrowing hair shafts, which is a central element of a mature hair follicle (Chuang et al., *J Invest Derm* 127:2098 (2007)). Others have shown that skin substitutes consisting of epithelial cells and modified mesenchymal cells can be used as transplantable grafts capable of inducing hair follicles (WO2011/160055A2).

U.S. patent application Ser. No. 2012/0095445 by Zheng, et al., describes methods and reagents for creating hair follicles in vitro from dissociated epidermal and dermal cells, which are cultured and passaged separately, then combined to form hair follicles which are subsequently implanted. Sonic hedgehog pathway agonists are used to increase the trichogenicity of the dissociated cells. This process is limited, however, since the hair follicles must be formed in vitro, then implanted.

US Patent Publication No. 2011/0321180 to Lee et al. discloses the formation of murine hair follicles from freshly isolated murine multipotential precursor cells from neonatal mice. Because the number of freshly isolated cells is limited, there is a need for regenerating skin using culture-expanded cells. Unfortunately, culturing pluripotent cells often results in a loss in the ability of the cells to differentiate into desired cell types.

Therefore, it is an object of the invention to provide compositions and methods for producing reconstituted skin and methods of use thereof where dissociated cells are implanted directly into the site where hair is desired, and hair follicles form in situ.

SUMMARY OF THE INVENTION

Reconstituted human skin containing cycling mature human hair follicles which produce normal pigmented hair shafts has been created. The reconstituted human skin contains a full subcutis layer, and hair follicles that form therein that grow in a distinctive pattern seen in the skin from which the cells are derived. The skin is created by obtaining multipotent and differentiated epidermal cells and differentiated dermal cells, culturing the epidermal and dermal cells/multipotent cells separately and separately passaging the proliferated cells, mixing the cells together to form a cell suspension, applying the suspension to an inert biocompatible substrate suitable for attachment of cells such as a slightly permeable silicone membrane, allowing the cells to attach to the substrate, typically about one to two hours, then applying the attached cells to full thickness wounds of small dimension. The ratio of multipotent and differentiated epidermal cells is in the range from 1:1 to 10:1. Areas to be implanted with cultured cells to form hair follicles are typically prepared using a one to two mm punch biopsy. The areas into which the cells are to be implanted may be as large as 0.5 to 2 $cm^2$ and between 0.6 and 0.8 cm deep, however. The substrate is secured to the site to insure the cells remain within the wound site. Reconstituted skin covering an area of 0.1-2 $cm^2$ may hold from 50-2000 mature hair follicles per $cm^2$.

Topical immunosuppressant delivered before or after placing the cells, by superficial injection, microneedles or topically, can be used to enhance survival and proliferation of the grafts.

Examples demonstrate preparation of cells on substrates, implantation into prepared sites, and formation of new functional hair follicles in mice. This mouse model is useful for studying human skin or hair follicle biology and pathology in pharmaceutical and academic laboratories, such as compound screening, studying skin carcinogenesis, testing drug effect on human skin and hair follicle physiology, and studying specific skin or hair follicle disorders.

DETAILED DESCRIPTION OF THE INVENTION

I. Definitions

The term "allogeneic" refers to tissue grafts that are genetically different although belonging to or obtained from the same species.

The term "autologous" refers to cells or tissues that are obtained from the same individual, where the donor and recipient are one and the same.

The term "xenogeneic" refers to tissues or cells belonging to individuals of different species.

"Dissociated cells" are cells that have been separated from other cells in a tissue, typically by digestion with an enzyme to break apart the extracellular matrix securing the cells to form the tissue.

The term "hair follicle" refers to the tubular mammalian skin organ that produces hair. A normal hair follicle contains a hair shaft, exhibits normal hair follicle (anagen, catagen, telogen) cycling, and sebaceous glands.

The term "hair shaft" refers to the filament growing from the deep follicle.

The term "dermal cells" or "dermal fibroblasts" refers to cells that surround and interact with the hair follicle. These cells have inherent follicle-inducing activity. Other dermal cells make up the dermis, or second layer of skin, which are responsible for generating the connective tissue that unites separate cell layers and allows the skin to recover from injury.

The term "epidermal cell" refers to the cells which constitute the outermost layer of the skin, composed primarily of keratinocytes as well as the epithelial cells which make up the hair follicle.

The term "keratinocyte" refers to the predominant cell type in the epidermis.

The term "melanocyte" refers to the melanin-producing cells located in the bottom layer of the skin's epidermis and in the bottom of the hair follicle that are responsible for skin pigmentation.

The term "passaged" refers to cells that have been subcultured or split to increase their number and grown under cultured conditions for extended periods of time. Each time the cells are transferred from one vessel to another is considered "one passage".

The term "sebaceous gland" refers to the oil glands that grow out from the upper follicle. They secrete an oily/waxy matter called sebum into the hair follicle canal which lubricates and waterproofs the skin and hair.

The term "dermal papilla" refers to cells that sit at the base of the follicle, forming a small, nipple-like body.

The term "dermal sheath" refers to the connective tissue lining the follicle.

The term "subcutis layer" refers to the deepest layer of the skin that is joined to the bottom of the dermis.

The term "isolated cells" is meant to describe cells that are in an environment different from that in which the cells naturally occur, such as dermal cells that are separated from a hair follicle.

The term "cohere" refers to the ability of cells to connect to each other and form a conglomerate.

The term "intact epidermis" refers to the epithelial outer layer of the skin. "Intact" refers to the fact that the epidermis has not been disrupted.

The term "full cutis layer" refers to the dermis.

The term "telogen" refers to the resting phase of the hair follicle, during which hair growth is absent.

The term "anagen" refers to the active growth phase of the hair follicle during which the hair shaft is growing.

The term "catagen" refers to a transition phase that occurs at the end of the anagen phase, which signals the end of the active growth of a hair.

"Cycling hair follicles" are hair follicles that undergo cycles of growth (anagen), regression (catagen) and rest (telogen).

The term "ROCK" refers to Rho kinase, which is a serine-threonine kinase that mediates various important cellular functions such as cell shape, by acting on the cytoskeleton. The addition of ROCK inhibitors to a cell culture medium can block apoptosis, thereby allowing for the selection of a specific population of cells that otherwise may not survive (Chapman et al., *J Clin Invest,* 120:2619 (2010)). Exemplary ROCK inhibitors include, but are not limited to, Y-27632.

"Alkaline phosphatase" (AP) is an enzyme that works most effectively in an alkaline environment, where it is responsible for dephosphorylating many types of molecules. The expression of this enzyme is regularly expressed in the dermal papillae.

The term "pilosebaccous unit" refers to the hair follicle and its sebaceous gland.

The term "skin appendage" refers to structures associated with the skin including, but not limited to, hairs, sweat glands, and sebaceous glands.

The term "immunoprivileged cells" refers to cells that are relatively resistant to immune responses, making rejection of non-histocompatible grafts less vigorous.

The term "neonatal cells" refers to multipotent, undifferentiated, and partially differentiated cells that are derived from newborn infant foreskins II. Production of Dissociated Cells for Implantation to Form Hair Follicles Sources of Cells Typically the skin progenitor cells are human dermal and epidermal cells Dissociated multipotent epidermal cells can be derived from human fetal scalp or human newborn foreskin. Primary Epidermal Keratinocytes; Normal, Human, Neonatal Foreskin can be obtained from the American Type Culture Collection, Product ATCC® PCS-200-010. Neonatal skin contains skin stromal cells that can differentiate into multiple cell types (i.e., multipotent cells). See Vishnubalaji, et al. *BMC Developmental Biology* 2012, 12:7. Differentiated epidermal cells are typically obtained by biopsy from the intended recipient.

Dissociated multipotent dermal cells can be derived from human fetal scalp or human neonatal foreskin. Human Dermal Fibroblasts, neonatal (HDFn) are also available from Cascade Biologics® cat# C-004-5C. Additional sources of epidermal cells include truncal skin, oral mucosa, and mesenchymal stem cells undergoing a mesenchymal to epithelial transition. Dissociated differentiated dermal cells are typically obtained from human adult scalp.

Other sources of multipotent cells include bone marrow or blood derived cells, and melanocytes, adipocytes, neural or endothelial procursers. These cells can also be generated from an iPS source.

The ratio of multipotent and differentiated epidermal cells is in the range from 1:1 to 10:1.

In the preferred embodiment, the differentiated cells are autologous—i.e., obtained by biopsy from the intended recipient, cultured and expanded outside the body, and reintroduced into the donor to form new hair follicles. This approach is advantageous because it reduces the risk of systemic immunological reactions stemming from biological incompatibility. It also reduces the risk of disease transmission associated with allogeneic tissue grafts, which originate from a different individual belonging to the same species. However, since it appears that hair follicles consist of immunoprivileged cells, allogeneic differentiated cells may be used when necessary. Over time, following implantation, these are typically replaced by the host's own cells.

Allogeneic melanocytes can also be delivered to the skin and thus the hair follicles by injection with the construct or separately into the surrounding skin or by mixing the melanocytes with the original cells.

Dissociation and Culturing of Cells

The separate populations of dermal and epidermal cells from the explant or donor tissue are dissociated into individual cells or aggregates containing small numbers of cells. Dissociation can be obtained using any known procedure, such as treatment with enzymes such as trypsin and collagenase, or by using physical methods of dissociation such as with a blunt instrument or by mincing with a scalpel to a allow outgrowth of specific cell types from a tissue.

Dissociated cells can be placed into any culture medium capable of supporting cell growth, including MEM, DMEM, and RPMI, F-12, containing supplements which are required for cellular metabolism such as glutamine and other amino acids, vitamins, minerals and useful proteins such as transferrin. Medium may also contain antibiotics to prevent contamination with yeast, bacteria and fungi such as penicillin, streptomycin, and gentamicin. In some cases, the medium may contain serum derived from cows, horses, or chickens. A particularly preferable medium for cells is a mixture of DMEM and F-12. Primary cultures of dissociated epidermal cells are preferably maintained in commercial medium supplemented with a Rho-associated protein kinase (ROCK) inhibitor. Exemplary ROCK inhibitors are Y-27632, ROK-beta and p160ROCK. The ROCK inhibitor is preferably used at a concentration of 10 µM or less (Rizzino, A., *Regen Med.*, 5(5):799-807 (2010)).

Culture conditions should be close to physiological conditions. The pH of the culture media should be close to physiological pH, preferably between pH 6-8, more preferably close to pH 7, even more particularly about pH 7.4. Cells should be cultured at a temperature close to physiological temperature, preferably between 30° C.-40° C., more preferably between 32° C.-38° C., and most preferably between 35° C.-37° C.

The dissociated epidermal cells and dissociated dermal cells are typically maintained and expanded in separate cultures. The separate cultures are passaged by removing the medium from confluent cells and adding trypsin to detach the cells from the cell culture flask. The resultant cell/trypsin mixture is then diluted in fresh growth medium and added to a new flask. This constitutes the first passage. The cells are then allowed to expand over the course of the next few days until they reach confluence again and the procedure can be repeated (second passage). Both dermal and epidermal cells are typically propagated separately up to the third passage for up to three weeks to increase the number of cells.

Application to Substrate

The expanded dermal and epidermal cells are combined, for example, in a 1:1 ratio, to produce a cell slurry, for example, in a cell culture medium such as DMEM/F12(1:1) (Gibco, Cat.#11039). Other ratios can be used, ranging from 1:2 to 1:10 epidermal to dermal cells. The cell slurry is subsequently transferred onto an inert biocompatible substrate. The substrate is preferably easily removed from the cells once the human skin is reconstituted. Various biodegradable materials can be used as the substrate such as polyesters like polylactic acid and polyglycolic acid, and proteins like collagen, gelatin, fibrin, and albumin. Other exemplary non-biodegradable substrate materials include carbon, silicon, or polytetrafluoroethylene. Preferred substrates include silicon membranes, a polyethylene terephthalate (PET) membrane (Invitrogen) or a BD Falcon cell culture insert with 3.0 µm pore size.

The cell suspension is applied to the substrate and then incubated at 37° C. for 1-2 hours, preferably 1 to 1.5 hours in a cell culture incubator, allowing the cells to adhere to form a cohesive mass of cells.

Implantation in Recipient

Areas to be implanted with cultured cells to form hair follicles are typically prepared using a one to two mm punch biopsy. The areas into which the cells are to be implanted may be as large as 0.5 to 2 $cm^2$ and between 0.6 and 0.8 cm deep. Alternatively, the mixed suspension of passaged cells may be injected directly into the site where hair is desired.

The substrate with dermal and epidermal cells adhered thereto is placed onto the undamaged musculature fascial plane at the base of the surgical wound with cells contacting the wound and with the substrate on top. The cells begin to form skin including skin appendages once the cells are applied to the surgical wound. It is believed that the combination of cells when present in the wound are able to reorient and generate cues that promote the proper formation of complex components of human skin including hair follicles and associated glands. In one embodiment, the reconstituted skin covers an area of 0.1-2 $cm^2$ and holds from 50-2000 mature hair follicles per $cm^2$.

Generally the substrate is secured with tape, staples or sutured. Sterile dressings can be applied to reduce infection.

A topical immunosuppressant such as TGF beta 1, TGF beta 2, ACTH, alpha MSH, Cyclosporine A or Rapamycin can be applied to the graft to decrease inflammation and rejection of the graft. The immunosuppressant is delivered before or after placing the cells, by superficial injection, microneedles or topically. Administration of immunosuppressant is particularly preferred when melanocytes are also administered, as discussed above.

As demonstrated by the examples, the reconstituted human skin on the mouse model contains cycling mature human hair follicles which produce normal pigmented hair shafts. The reconstituted human skin on the mouse model contains a full subcutis layer, and the hair follicles that form therein grow in a distinctive pattern seen in the skin from which the cells are derived. The reconstituted skin can remain human in its morphology and behavior for over six months. The reconstituted skin is better vascularized and more long-lived than transplanted skin xenografts.

Reconstituted Human Skin

The reconstituted human skin contains cycling mature human hair follicles which produce normal pigmented hair shafts. In certain embodiments, the reconstituted human skin contains a full subcutis layer, and the hair follicles that form therein grow in a distinctive pattern; that is, the follicles do not appear to form at random but they have a defined relationship to one another.

The salient events of hair-follicle morphogenesis can be summarized as follows: formation of epidermal platform then dermal condensations→epithelial invagination to form the follicular wall→formation of dermal papillae (DP) at the base of the follicle→→molecular differentiation of hair-shaft components→ability to grow and cycle while preserving stem cells and DP for the next cycle→ability to regenerate.

As demonstrated by the examples, the disclosed method leads to the production of reconstituted skin containing hair follicles having the following characteristics:

1. The proximal end of the skin appendages shows a follicle configuration, with epithelial filament coming out of the distal end of the follicle and dermal papillae sitting at the base of the follicle.

2. The implant has proliferating cells (Transient Amplifying, TA, cells) positioned proximally and differentiating cells positioned distally, forming a proximal-distal growth mode.
3. The follicle is made of concentric layers of outer and inner root sheath, cuticle, cortex, and medulla. Although in different hair types variations can occur with the basic design, all follicles have a distinct internal root sheath (Henle and Huxley) and companion layers.
4. The product of a follicle, the shaft, is made of unique molecular constitution.
5. The follicle is associated with sebaceous glands.
6. A follicle has the machinery to shed an old shaft while preserving stem cells and DP for the next cycle.
7. Inherent in the follicle is the ability to regenerate a new hair organ through repeated hair cycles.

Preferably, the reconstituted skin includes three main layers: epidermis, cutis or dermis, and subcutis. The epidermis is composed mostly of keratinocytes. Penetrating the epidermis are sweat glands and hair shafts. The epidermis sits on the dermis while the dermis sits on the subcutis. The subcutis is the deepest layer of the skin and contains lipocytes, which produce lipids for the subcutaneous tissue to make a layer of fat that cushions muscles, bones and inner organs. It acts as an insulator and an energy reservoir.

The hair shaft of the reconstituted skin can generally extend from the dermis out onto the epidermis. The dermal part of the hair follicle has two main parts: the dermal papilla and the dermal sheath. By definition, mature hair follicles have dermal papillae at the base or bulb, proliferating cells positioned proximally, and differentiating cells positioned distally, thereby facilitating a proximal-distal growth mode. The follicle is composed of concentric layers of outer and inner root sheath, cuticle, cortex and medulla. The shaft, which is the product of the follicle, has a unique molecular constitution. The follicle is also associated with sebaceous glands, and has the ability to regenerate a new hair organ through repeated cycles of growth (anagen), regression (catagen) and quiescence (telogen).

The present invention will be further understood by reference to the following non-limiting examples.

EXAMPLE 1

Implantation of Cultured Cells to Form Hair Follicles In Situ

Materials and Methods
Animals

"Nude/nude" (or "nu/nu") mice are homozygous for a genetic mutation that cripples the immune system, due primarily to a greatly reduced number of T cells. This mutation also renders the mice phenotypically hairless, but simultaneously makes them suitable recipients for various non-self types of tissue and tumor grafts, as their immunodeficiency prevents them from rejecting the grafts.

"NOD/SCID" mice are albino mice that are heterozygous for a gene that makes them susceptible to autoimmune insulin dependent diabetes (non-obese diabetic or NOD), and for a gene affecting T- and B-lymphocyte development (severe combined immunodeficiency, or SCID). These mice are suitable recipients for various types of tissue and tumor grafts, as their immunodeficiency prevents them from rejecting the grafts.

Cells and Cell Culture. Dissociated epidermal cells were derived from human fetal and adult scalp, as well as from human newborn foreskin. Dermal cells were derived from fetal and adult scalp. After isolation of cells from tissues, primary cultures containing dermal cells were maintained in culture. Primary cultures of epidermal cells were maintained in commercial medium plus Rho-associated protein kinase (ROCK) inhibitor, Y27632. Both dermal and epidermal cells were propagated separately up to the third passage for up to three weeks, and were then mixed in a 1:1 ratio to produce a cell slurry in a total volume of 150 µl of DMEM/F12 (1:1) (Gibco, Cat.#11039). The cell slurry was subsequently transferred onto a silicon membrane (Invitrogen), and incubated at 37° C. for 1-1.5 hours in a cell culture incubator, allowing the cells to adhere to the membrane.

Skin Grafts. Full-thickness skin was removed from the back of immunodeficient nude/nude or NOD/SCID mice to make a wound, and the silicon membrane with adherent cells was placed onto the undamaged musculature fascial plane at the base of the surgical wound with cells contacting the wound and the silicon membrane on top. One or two grafts were placed on each mouse and the membrane was subsequently sutured to the host skin. A sterile dressing with ointment was applied over the wound and the mice were wrapped with sterile tape and monitored over the course of the following 12-14 weeks.

Histological Analysis

At the end of this period the regenerated tissue was examined by dissecting light microscopy and then sectioned for high magnification light microscopy using hematoxylin and eosin stains. H&E staining (histological analysis) was carried out according to standard protocol. Briefly, 10 µm sections made from frozen block were fixed in 10% formalin, washed with 1×PBS, incubated with hematoxylin for 3 minutes, washed by distilled water, then incubated with eosin for 30 seconds. The stained sections were washed and dehydrated by incubation with 70%, 90% and 100% ethanol for 3 minutes, respectively. Dehydrated sections were rinsed in xylene, mounted using xylene-based mounting medium, and then examined by light microscopy.

Alkaline Phosphatase (AP) staining. AP staining was carried out on 6 week and 12 week old grafts according to the manufacturer's protocol (Roche NBT/BCIP stock solution, Cat# 11 681 451 001). Briefly, 10 µm sections made from frozen blocks were rinsed in PBS, and fixed in ice cold acetone for 10 minutes. The fixed sections were washed twice for 5 minutes each time in 1×PBS solution, then left in AP buffer (0.1M Tris-HCL, pH 9.5, 0.1M NaCl, 0.05M $MgCl_2$) for 5 minutes. The freshly prepared staining solution (200 µl NBT/BCIP stock solution in 10 ml AP buffer) was applied to the fixed section for around 5-30 minutes. A positive AP reaction generates dark blue staining which should be monitored by microscope every 5 minutes to determine the incubation time. After dark blue staining appeared, the staining solution was removed and the section was washed. Then, the section was counter stained. with eosin for 30 seconds, followed by dehydration with ethanol, and mounted with a glass cover-slip using a xylene-based mounting medium.

Analysis of grafts with GFP expressing cells. In order to produce GFP-expressing virus, 293 cells at 80% confluence were transfected with GFP-expressing retrovirus vector using Fugene HD transfection reagent. The virus-containing medium was collected every 24 hours over the next three days and stored at −80° C. For the infection, the frozen medium was thawed, centrifuged for 5 minutes at 1500 rpm, and the resulting supernatant was then mixed with polybrene (8 µg/ml). This mixture was used to infect 80% confluent cultured foreskin keratinocytes or cultured fetal scalp dermal cells at 6 ml of virus per T75 flask. After three hours of incubation, the infection medium was removed and replaced with normal growth medium.

The following day, cells were collected for grafting and the cultured foreskin keratinocytes infected with GFP-expressing virus were combined with wild-type dermal cells, while the cultured dermal cells infected with GFP-expressing virus were combined with wild-type foreskin keratinocytes to produce a cell slurry. The cell slurry was transferred onto a silicon membrane and incubated at 37° C. for 1-1.5 hours to form a graft construct. The construct was grafted onto the mice, and the grafts were monitored and harvested after 12 weeks. A thin layer of skin dissected from the graft was examined by fluorescence microscopy.

Immunofluorescence Analysis. Immunofluorescence analysis was carried out by standard protocol. 10 µm sections made from frozen blocks were fixed in 4% paraformaldehyde/PBS for 10 min, washed in PBS, and incubated with blocking buffer (10% donkey serum+2% BSA in PBS) for 1 h at room temperature. Primary antibodies against basement membrane markers (rat anti-FITC conjugated (CD49) α6-integrin (Stem Cell, cat. 10111)), epidermal cells or basal cell layer markers (mouse anti-human pan-cytokeratin (BD, cat. 550951)), or mesenchymal (dermal) cell markers (rabbit anti-vimentin (Cell Signaling, cat. 3932)) were then added for overnight incubation at 4° C. The following day, the sections were washed in PBS, and incubated with secondary antibodies for 1 hour. The sections were mounted using DAPI containing mounting medium (Vector Laboratory) and expression was analyzed by confocal microcopy.

Results

Skin Grafts from Dissociated Tissue Culture Expanded Human Cells Produce Hair Follicles.

Mice were monitored after surgery. Pigmented skin formed 4 weeks after grafting. At 12 weeks, hair shafts emerging from the skin surface were clearly visible by eye and continued to grow until 14 weeks post-graft. New skin and hair follicles formed 80% of the time and the skin produced covered an area range of 0.5-2 cm² and held 50-1000 mature hair follicles. Robust pigmented hairs were clearly visible in the grafted area. The fact that the hairs were pigmented is a direct indication that the epidermal cell culture contains melanocytes, and that the reconstituted hair follicles resulted from the grafted human cells, since NOD/SCID host mice do not produce pigmented hair, and nude/nude mice do not produce any hair at all.

Regenerated Human Hair Follicles Cycle and have Mature Shafts Associated with Sebaceous Glands and Dermal Papillae.

To further characterize the reconstituted hair shafts, individual follicles were isolated under a dissection microscope. The regenerated hair follicles exhibit mature features, namely, different layers including a pigmented hair shaft, an inner and an outer root sheath. The follicle was associated with sebaceous glands and dermal (papillae . Follicles in the anagen phase with a strong pigmented shaft bulb area attached to a cupped dermal papilla were observed, as well as telogen-like follicles with much less pigmented shafts and dermal papillae which are located at the tip of the hair follicle. Significantly, the presence of both anagen and telogen follicles in the same graft indicates that the regenerated hair follicles are cycling. The ability of a hair follicle to cycle is an important criterion defining a mature hair follicle. Sections of skin containing follicles were further analyzed by Hematoxylin and Eosin (H&E) staining, which demonstrated cycling hair follicles forming sebaceous glands and mature dermal papillae.

For even further examination of hair cycling, hairs were trimmed short to allow hair cycle phases to be observed. Regrowth of hairs one month after trimming was observed.

Identification of Dermal Papillae by Alkaline Phosphatase (AP) Staining in the Reconstituted Hair Follicles.

Alkaline phosphatase (AP) is a marker distinguishing dermal papillae from other dermal fibroblasts. To further characterize the regenerated hairs and skin, AP staining was carried out on 6 week and 12 week old grafts. Papillae with AP positive blue staining were located at the proximal tip of early stage (stage 3) hair follicles of 6 week old grafts, and were cupped by a mature anagen hair follicle of the 12 week old grafts. Taken together, these data indicate that the reconstituted hair follicles have mature shafts associated with sebaceous glands and dermal papillae.

Reconstituted Hair Follicles Incorporate Cultured Green Fluorescent Protein (GFP)-expressing Cells.

To demonstrate that the regenerated hair follicles were formed from grafted cells, cultured foreskin keratinocytes were infected with a GFP-expressing retrovirus vector prior to grafting, allowing the grafted cells to be traced by fluorescence microscopy. Twelve weeks after grafting, thin layers of skin were dissected from the graft and were analyzed by fluorescence microscopy. Mature follicles associated with sebaceous glands could be seen from the phase contrast image. All epidermal parts, including sebaceous glands, and the interfollicular epidermis were fluorescent green, indicating that they originated from GFP-expressing keratinocytes. By contrast, all dermal parts including papillae were negative for GFP.

In addition, fetal scalp dermal cells infected with GFP-expressing retrovirus were combined with wild-type epidermal cells and grafted onto mice. Twelve weeks later, the grafted tissue was harvested and analyzed for GFP expression under a fluorescent microscope. All dermal portions were positive for GFP (including the dermal papilla), while all the epidermal areas of the graft were negative for GFP. These data strongly support the conclusion that the reconstituted skin and hair follicles formed from the implanted dissociated cultured human epidermal and dermal cells.

Regenerated Hair Follicles and Epidermis are Reconstituted from Cells of Human Origin.

The presence of protein markers characteristic of mature human hair follicles was analyzed by immunofluorescence microscopy to reconfirm that the regenerated hair follicles and epidermis are human in origin. Cytokeratins are proteins that are typically expressed in the intracytoplasmic cytoskeleton of epithelial tissue. Pan-cK specifically is a cytokeratin marker that is useful for identifying human epidermal cells. Vimentin is an intermediate filament that is expressed in mesenchymal cells, and is a marker that is useful for identifying human dermal cells. Integrins are receptors that facilitate the attachment between a cell and the tissues that surround it. DAPI is a fluorescent stain that binds strongly to A-T rich regions in DNA. Skin sections from 6 month grafts were exposed to antibodies against Pan-cK and vimentin. Antibodies against α6-integrin were used to mark the border between the epidermis and the dermis, while DAPI was used to label the nuclei. The expression of two human-specific markers (Pan-cK and vimentin) in mouse grafts indicated that the regenerated hair follicles and epidermis harvested from the mice are derived from human cells.

It can be concluded from these results that regenerated human hair follicles can be successfully regenerated by grafting dissociated and cultured fetal scalp epidermal cells or foreskin keratinocytes. Furthermore, the regenerated hair follicles are capable of forming mature hair shafts associated with sebaceous glands and dermal papillae.

The animals generated in this example are useful in the study of human disease and for screening of compounds for treatment of normal or diseased skin or hair. The skin used to provide the cells may be obtained from a human with a disease to be studied, or for which a compound is to be screened for an effect. In this method for making full thickness human skin on the back of an immunoincompetent animal using normal human skin, a suspension of a mixture of cultured and passaged human multipotent and differentiated dermal and epidermal cells is prepared, adhered to an inert biocompatible substrate suitable for application to wounds in skin, wounds at a site where skin is desired are made on the animal, and the cell-substrate is applied, cell side to the wound. Once the skin and/or hair follicles have formed, compounds to be tested can be applied to the skin and compared to untreated skin, or areas formed from diseased skin cells can be compared to areas formed from normal skin cells.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A composition for generating hair follicles, wherein said composition comprises a mixture of cultured and passaged cells adhered to an inert biocompatible substrate suitable for application to wounds, wherein said mixture of cells contains differentiated dermal and epidermal cells derived from adult human scalp, and further contains multipotent dermal and epidermal cells that are not derived from adult scalp.

2. The composition of claim 1, wherein the cells are from different individuals.

3. The composition of claim 1, wherein the substrate is a semi-permeable polymeric or silicon membrane.

4. The composition of claim 1, wherein the dermal and epidermal cells are present in said mixture at an approximate 1:1 ratio.

5. The composition of claim 1, wherein said mixture of cells further comprises melanocytes.

6. The composition of claim 1, wherein said cultured and passaged cells have been cultured in the presence of a Rho-associated protein kinase (ROCK) inhibitor.

7. The composition of claim 1, wherein said multipotent dermal and epidermal cells that are not derived from adult scalp are from a neonatal tissue.

8. The composition of claim 1, wherein the cells are immersed in a cell culture medium.

9. A method for preparing the composition of claim 1, said method comprising adhering a mixture of cultured and passaged cells to an inert biocompatible substrate suitable for application to wounds, wherein said mixture of cells contains differentiated dermal and epidermal cells derived from adult human scalp, and further contains multipotent dermal and epidermal cells that are not derived from adult scalp.

10. The method of claim 9, wherein the cells are from different individuals.

11. The method of claim 9, wherein the substrate is a semi-permeable polymeric or silicon membrane.

12. The method of claim 9, wherein the dermal and epidermal cells are present in said mixture at an approximate 1:1 ratio.

13. The method of claim 9, wherein said mixture of cells further comprises melanocytes.

14. The method of claim 9, wherein said cultured and passaged cells have been cultured in the presence of a Rho-associated protein kinase (ROCK) inhibitor.

15. The method of claim 9, wherein said multipotent dermal and epidermal cells that are not derived from adult scalp are from a neonatal tissue.

* * * * *